United States Patent
Shaak

(12) 
(10) Patent No.: US 6,228,852 B1
(45) Date of Patent: *May 8, 2001

(54) TRANSDERMAL APPLICATION OF NATURALLY OCCURRING STEROID HORMONES

(76) Inventor: Carolyn V. Shaak, 1093 Beacon St., Brookline, MA (US) 02146

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/889,529

(22) Filed: Jul. 8, 1997

Related U.S. Application Data

(60) Provisional application No. 60/021,894, filed on Jul. 12, 1996.

(51) Int. Cl.[7] .................................................. A61K 31/56
(52) U.S. Cl. ......................... 514/178; 514/170; 514/874; 514/937; 424/400
(58) Field of Search .................... 424/449, 400; 514/170, 178, 874, 937

(56) References Cited

U.S. PATENT DOCUMENTS

| | | | | |
|---|---|---|---|---|
| 4,150,128 | * | 4/1979 | Jasionowski | 424/240 |
| 4,177,267 | * | 12/1979 | Herschler | 424/238 |
| 4,436,738 | * | 3/1984 | Bequette | 424/238 |
| 4,542,129 | * | 9/1985 | Orentreich | 514/178 |
| 4,762,717 | * | 8/1988 | Crowley, Jr. | 424/425 |
| 5,059,426 | * | 10/1991 | Chiang | 424/449 |
| 5,407,944 | * | 4/1995 | Goldman | 514/310 |
| 5,460,820 | | 10/1995 | Ebert et al. | |
| 5,709,878 | * | 1/1998 | Rosenbaum | 424/449 |
| 5,728,688 | * | 3/1998 | Labrie | 514/178 |

FOREIGN PATENT DOCUMENTS

| | | |
|---|---|---|
| 0723775A1 | 7/1996 | (EP) . |
| WO 94/16709 | 4/1994 | (WO) . |
| WO 97/03676 | 6/1997 | (WO) . |

OTHER PUBLICATIONS

Marslew, U. et al., Progestogens: Therapeutic and Adverse Effects in Early Post–Menopausal Women, Abstract, Maturitas, 13(1), pp. 7–16 (1991), Entire Abstract.

Regine Sitruk–Ware, "Percutaneous and Transdermal Oestrogen Replacement Therapy", *Annals of Medicine*, 25:77–82, 1993.

* cited by examiner

Primary Examiner—Thurman K. Page
Assistant Examiner—T. Ware
(74) Attorney, Agent, or Firm—Clark & Elbing LLP

(57) ABSTRACT

The invention features a physiologically acceptable cream that contains estrogen, progesterone, and testosterone molecules that are identical to the estrogen, progesterone, and testosterone molecules naturally produced by the human body. The cream may be self-administered to the skin and is useful as a means of hormone replacement therapy, which may begin at around the time of menopause.

20 Claims, 2 Drawing Sheets

TRANSDERMAL APPLICATION OF NATURALLY OCCURRING STEROID HORMONES

CROSS REFERENCE TO RELATED APPLICATIONS

This application is a continuation-in-part of Provisional Patent Application Ser. No. 60/021,894, filed Jul. 12, 1996.

BACKGROUND OF THE INVENTION

This invention relates to hormone replacement therapy.

Progesterone is a steroid hormone that is produced by the ovaries during a woman's child-bearing years. Progesterone is also made, although in smaller amounts, by the adrenal glands in both sexes and by the testes in males. An astonishing variety of physiological functions are mediated by progesterone (See e.g., Lee, 1993, Natural Progesterone, BLL Publishing, Sebastopol, Calif.). For example, progesterone, which surges following ovulation, maintains the secretory endometrium and thus, helps to ensure the survival of the embryo and fetus. It also acts as a diuretic, an antidepressant, and as a precursor of corticosteroids and of other sex hormones, notably estrogen and testosterone. There is also evidence that progesterone affords protection against loss of libido, osteoporosis, endometrial cancer, breast cancer, and fibrotic cysts.

When the child-bearing years draw to a close, every woman experiences a decline in the production of progesterone, and consequently, a decline in all of the hormones that are synthesized from progesterone. This decline significantly and negatively affects both life-span and quality of life (Ettinger, 1996, Obst. and Gyne. 87:6–12; Karlberg et al., 1995, Acta. Obstet. Gynecol. Scand. 74:367–372). In addition to the uncomfortable symptoms, such as hot flashes, that are frequently experienced at around the time of menopause, there is an increase in the prevalence of life-threatening conditions, including heart disease, osteoporosis, and brain ischemia (more commonly called a "stroke"; Hunt et al., 1990, Br. J. Obstet. Gynecol. 97:1080–1086). These conditions exact a high personal price and consume significant medical resources. Postmenopausal osteoporosis, the most common metabolic bone disorder in the United States, is the underlying cause of over 1.3 million fractures, at an estimated cost of over $10 billion annually.

Currently, the most common form of treatment for post-menopausal osteoporosis, as well as the other complex physiological conditions associated with menopause, is oral administration of estrogen, either alone or in combination with synthetic progestins. It is estimated that women under the age of 85 who adhere to a program of hormone replacement therapy (HRT) reduce their risk of having a fatal stroke or heart attack by 50–60% (Paganini-Hill et al., 1988, Br. Med. J. 297:519; Henderson et al., 1988, Am. J. Obstet. Gynecol. 159:312). Not only does overall longevity increase (Folsom et al., 1995, Am. J. Public Health 85:1128–1132), but quality of life is improved by HRT as measured by indices of mood, sleep quality, sexual satisfaction, memory, and skin tone, and by bone densimetry (Purdic et al., 1995, Br. J. Obstet. Gynaecol. 102:735–739; Sherwin, 1991, J. Clin. Endocrinol. Metab. 72:336–343; Kimura et al., 1995, Horm. Behav. 29:312–321; Jaliman, 1995, Menopause Mgmt. July/Aug. 34–38; Genant et al., 1989, Am. J. Obst. Gynecol. 161:1842).

There are substantial side effects associated with current hormone replacement therapies (Lee supra; see also Darj, 1992, Maturitas 15:209; Glueck, 1995, J. Lab. Clin. Med. 123:59; Hillard, 1992, Fert. Steril. 58:959–963). For example, administration of unopposed estrogen has been associated with an increased risk of endometrial hyperplasia and adenocarcinoma in women with an intact uterus (Samsioe, 1992, Am. J. Obstet. Gynecol. 166:1980–1985; Ziel et al., 1975, N. Engl. J. Med. 293:1167–1170) and with an increased incidence of breast cancer, regardless of whether or not the patient has had a hysterectomy. Therefore, postmenopausal women who have had breast or endometrial cancer, or who have a strong family history of these cancers, are generally considered poor candidates for many currently prescribed hormone replacements.

Similarly, synthetic progestins are contraindicated for women with known or suspected malignancies of the breast or genital organs, and are associated with a number of undesirable side effects. For example, medroxyprogesterone acetate, a commonly prescribed progestin, carries warnings that it may cause or contribute to pulmonary embolism, cerebral thrombosis, mental depression, nausea, insomnia, fluid retention, migraine headache, renal dysfunction, weight gain, and acne. It is, therefore, not surprising that 30% of the patients for whom HRT is prescribed will never even fill their prescriptions (Ravnikar, 1987, Am. J. Obstet. Gynecol. 156:1332).

In addition to undesirable and potentially lethal side effects, several other factors contribute to the underutilization of HRT world-wide. These include the fear of contracting cancer, the concept that medication is given only to treat illness, rather than to promote wellness, and the related psychological barrier constructed by those who believe that following a program of HRT represents a woman's personal failure to manage her own feminity without chemical intervention.

SUMMARY OF THE INVENTION

The invention features a method of hormone replacement therapy, whereby a combination of native estrogen, native progesterone, and native testosterone are administered transdermally to a patient in need of such therapy. The hormones are synthesized from compounds obtained from a plant source (preferably such as a soybean or yam plant), micronized, and dissolved in a physiologically acceptable cream that can be applied to the skin. Preferably the cream is self-administered to areas of the skin that overlie fatty tissue. Examples of such areas are the lower abdomen and inner thighs. Persons most likely to benefit from the method of the invention are women who are approaching, or who have already come to, the end of their child-bearing years. However, hormone deficiencies caused by events other than menopause can also be treated by the invention.

Preferably, the ratio, by weight, of estrogen to progesterone to testosterone is approximately 1–5 to 10–500 to 1–5, respectively. Most preferably, the ratio, by weight of estrogen to progesterone to testosterone is 1 to 200–250 to 1, most preferably 1 to 250 to 1. The concentration of estrogen in the cream may range from 0.1 to 10 mg/teaspoon, the concentration of progesterone may range from 20 to 2,000 mg/teaspoon, and the concentration of testosterone may range from 0.1 to 10 mg/teaspoon. Preferably, a teaspoon of cream will contain 2–6 mg estrogen, 600–1000 mg progesterone, and 2–6 mg testosterone. More preferably, a teaspoon of cream will contain 4 mg estrogen, 800 mg progesterone, and 4 mg testosterone. The cream may be applied one or more times per day, fourteen or more days per month. Preferably, the site of application is varied.

The invention preferably employs a physiologically acceptable cream consisting of native estrogen, native progesterone, and native testosterone. The cream may also contain an adrenal androgen, such as DHEA (dehydroepiandrosterone), which is produced by the adrenal cortex. A cream that contains native DHEA in addition to the three native sex hormones would be capable of replenishing all of the hormones that normally decline at around the time of menopause.

As described below, considerable confusion has been generated by the improper use of the terms progestin and progesterone in the literature. Herein, and as is correct, progestins are defined as compounds, other than natural progesterone, that are able to sustain the human secretory endometrium.

By "estrogen" is meant any natural substance that induces estrogenic activity. Natural estrogens include estradiol, estrone, and their metabolic product, estriol. The estrogen may be administered as a conjugate i.e., as a sodium salt of the sulfated esters of estrogenic substances.

By "native estrogen, native progesterone, and native testosterone" is meant compounds that are molecularly identical to the estrogen, progesterone, and testosterone molecules naturally produced by the human body.

By "around the time of menopause" is meant at around the time menstruation ceases, which most frequently occurs at the close of the child-bearing years.

DETAILED DESCRIPTION

Figure 1:
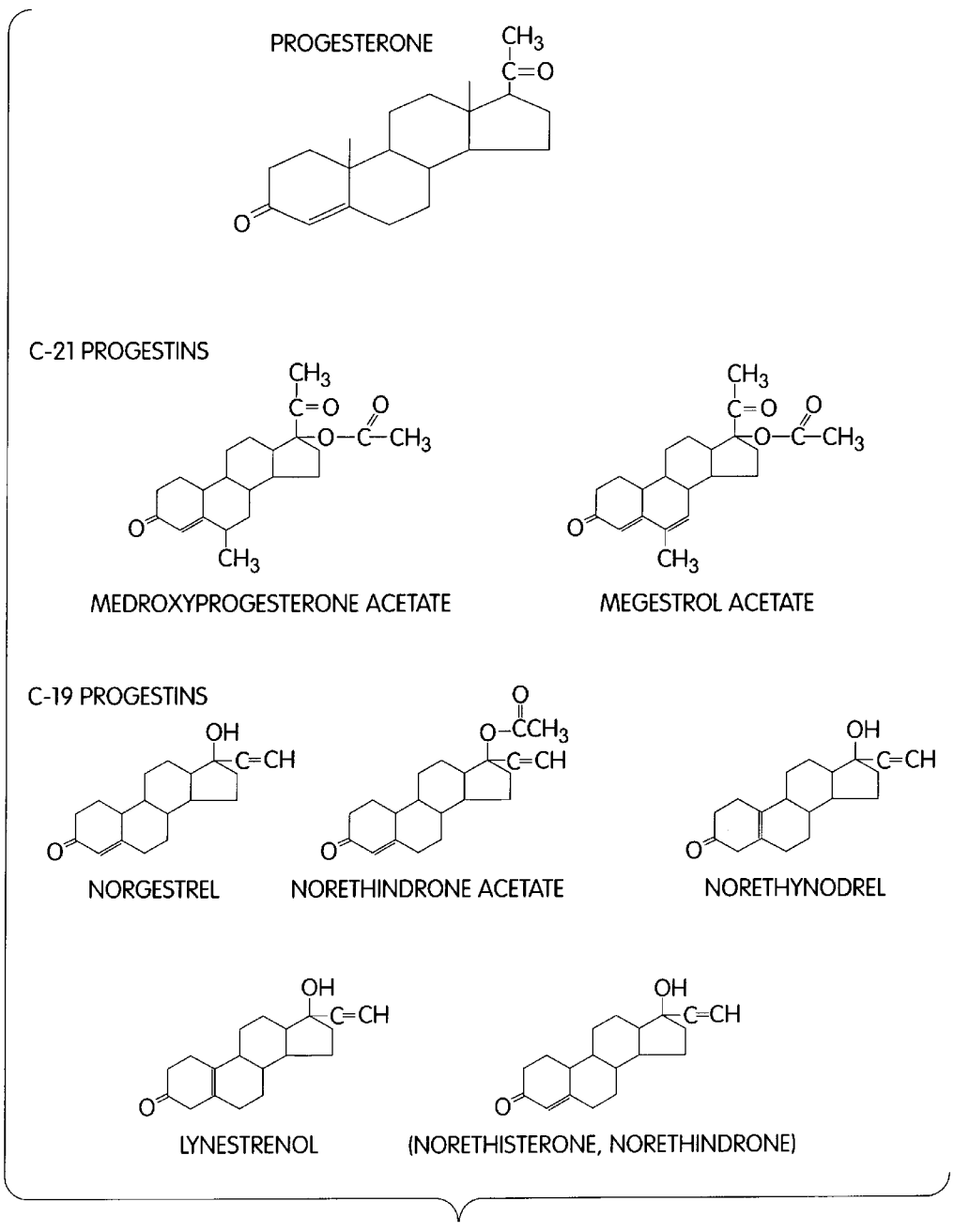
FIG. 1 is a schematic representation of the molecular structures of naturally-occurring (i.e. native) progesterone, and synthetic progestins.

Distinction Between the Compounds Employed in the Invention and Those Currently in Use as Hormone Supplements There is a wide-spread failure among physicians and other skilled artisans to fully appreciate the difference between progestins and progesterone. Progestins are often defined as compounds able to sustain the human secretory endometrium, and since progesterone performs this function, progesterone is often thought to be a progestin. This is incorrect. Progesterone is a steroid hormone that is made naturally by the body. In contrast, progestins are chemically synthesized ex vivo. Furthermore, synthetic progestins, of which there are many, differ from the one naturally occurring progesterone both structurally (FIG. 1) and functionally.

The differences between the chemical structures of progestins and natural progesterone significantly affect their biological activity. Synthetic progestins are not capable of performing many of the beneficial biological functions performed by natural progesterone. In fact, progestins and progesterone often mediate opposing events. For example, natural progesterone is necessary for the survival and development of the embryo, while PROVERA®, the most commonly prescribed synthetic progestin, increases the risk of early abortion and congenital deformities of the fetus. In addition, progestins and progesterone differentially affect systems other than the reproductive system. For example, natural progesterone is a diuretic, causing sodium diuresis with a secondary increase in the rate of aldosterone excretion. Thus, progesterone may act as an "anti-aldosterone," and thus afford protection against hypertension. In contrast, synthetic progestins increase sodium and water retention, and thereby contribute to hypertension.

Source of the Hormones Used in the Compositions of the Invention

The hormones of the invention are derived from a vegetable plant, such as a soybean or yam plant. This plant produces the sterol, diosgenin, which can be converted to natural progesterone. Thus, the hormones used in this invention are synthesized, not merely extracted, from the plant source. They are "natural" in the sense that they are molecular carbon copies of ovarian steroid hormones. The methods by which the diosgenin is isolated and biochemically converted to progesterone, estrogen, and testosterone are well known to skilled artisans.

Mode of Administration

Micronized native progesterone, estrogen, and testosterone are dissolved in propylene glycol and admixed into an almond extract base cream that is suitable for application to the skin. The cream can be self-administered, preferably by application to sites where relatively thin skin overlies fatty tissue. More preferably, the cream is applied to a number of different sites in turn; the patient applies the cream to the first site for several days to several weeks, then to a second site for a comparable period of time, and so on, eventually returning to the "first" site of application.

As a result of the administration described above, the fatty tissue itself becomes a reservoir for the applied hormones, which closely simulates the natural primary source of these hormones, i.e. the premenopausal ovary. Transdermally applied hormones of the invention become subject to natural feed-back mechanisms: they are not released from the fat reservoir if blood hormone levels are abnormally high. Consequently, transdermal application of steroid hormones, and their release from the fat reservoir, results in a steady-state level of hormones in the blood serum.

Dosage

Figure 2A:
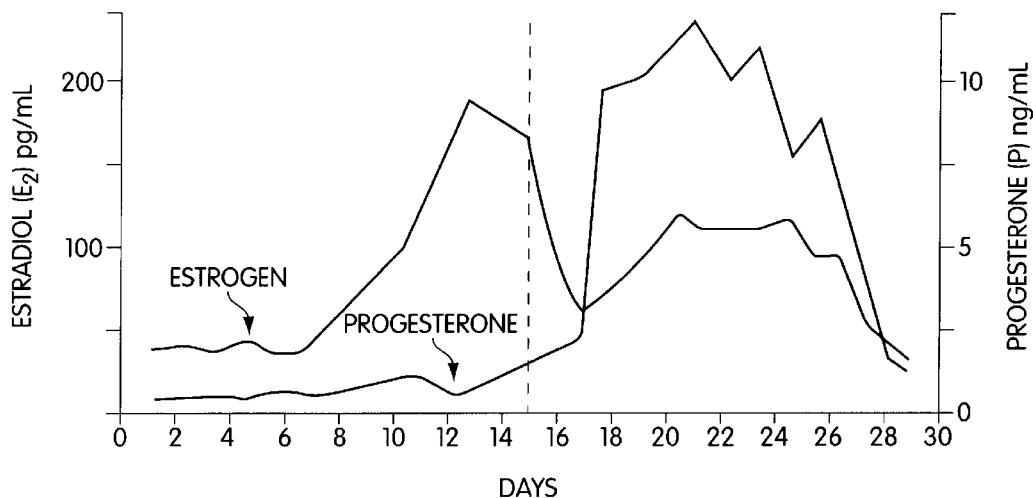
FIG. 2A is a line graph representing the blood serum levels of estradiol (pg/ml) and progesterone (ng/ml) over the course of a typical menstrual cycle.
Figure 2B:
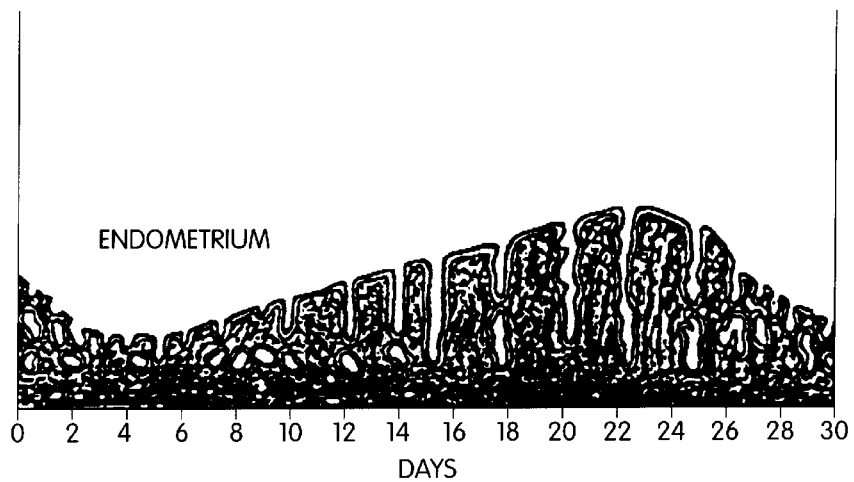
FIG. 2B is a schematic representation of the thickness of the human endometrium over a period of time that corresponds with that shown in FIG. 2A.

Generally, an effective dose of the hormones of the invention will be the dose that is sufficient to restore human serum levels of these hormones to values found in the early luteal phase in premenopausal ovulatory women (FIG. 2A and Table 1) and to maintain the endometrium at approximately the same thickness as on day 6 of the menstrual cycle (FIG. 2B).

The hormone-containing cream can be packaged, for example, in a pump dispenser so that one pump would deliver approximately one quarter teaspoon containing 1 mg estrogen, 200 mg progesterone, and 1 mg testosterone. Alternatively, the cream can be packaged in a tube or a jar containing approximately 325 mg/ounce of hormones in the ratio described above (estrogen to progesterone to testosterone at 1 to 200 to 1).

TABLE 1

|  | Premenopausal Circulating Levels | Postmenopausal Circulating Levels | Peak Circulating Levels | Trough Circulating Levels |
| --- | --- | --- | --- | --- |
| Estrogen | 30–400 pg/ml | <30 pg/ml | 80–190 pg/ml | 60–150 pg/ml |
| Progesterone | 0.1–16 ng/ml | <0.1 ng/ml | 1.5–4 ng/ml | 1–2 ng/ml |
| Testosterone | 3–100 pg/dl | <10–30 pg/dl | 30–50 pg/dl | 30–50 pg/dl |

The circulating levels of the hormones of the invention can be determined by standard laboratory methods. To ensure that the circulating levels of hormones are reasonably stable, a blood sample can be obtained and tested at two time points after the cream has been administered. For example, a sample can be tested 12 hours after administration of a once daily dose, at which time hormone levels should be at their peak, and again one hour before administration of the next daily dose, at which time the hormone levels should be at their lowest, or "trough level." If the circulating levels greatly exceed or fall below those shown in Table 1, the physician and patient may consider changing the frequency of application.

Preferably, the levels of circulating hormones will be in the following ranges: estrogen (e.g., estradiol) at 70–150 pg/ml, progesterone at 2–4 ng/ml, and testosterone at 30–50 nmol/ml. When progesterone is produced by the ovary it is subsequently embedded in a protein envelope consisting of cortisol binding globulin (CBG). Only 2–10% of progesterone circulates in the bloodstream unbound. Similarly, estrogen is embedded in sex hormone binding globulin (SHBG). It is not presently known whether progesterone absorbed transdermally acquires a CBG carrier envelope or whether it binds temporarily to fat soluble components of cell membranes, such as those of erythrocytes, for transport through the circulatory system. Thus, it is possible that measurements, e.g. measurements of plasma progesterone levels, may not accurately reflect the amount of progesterone available. Therefore, ultimately, dosage will be determined by the results achieved. Since natural progesterone is notable for its freedom from side effects, reasonable latitude in dosing carries little, if any, risk.

The administration of the hormone-containing cream of the invention may also be varied over time. This is preferable for at least two reasons. First, as shown in FIG. 2A, production of progesterone by the ovary varies considerably, reaching approximately 20 mg/day on days 18–26 of the menstrual cycle. In order to approximate normal production of progesterone, perimenopausal patients may apply a larger dose of the cream from day 12 to day 26 of the menstrual cycle and then cease application for approximately five days, during which time menstruation will usually occur. The second reason for altering the application of the cream with time is to prevent down-regulation of the cellular receptors that bind the hormones. Continued exposure of these receptors to their ligands, as is generally true for receptor-ligand pairs, results in decreased expression of the receptors and thereby, decreased effectiveness of the ligand. Thus, even postmenopausal women should be advised to cease application of the hormone-containing cream for at least five days each month.

Advantages

Transdermal application of a novel combination of hormone supplements, which are identical to the hormones produced by the functioning ovary, provides an effective, simple, safe, and affordable way to replenish these hormones.

One of the chief advantages of applying hormones that are molecular carbon copies of those produced naturally by the body is that they have many fewer side effects than the synthetic compounds currently used for hormone replacement therapy. Perhaps the greatest fear of taking oral doses of synthetic progestins is the fear of contracting cancer. These fears will be allayed by the findings that progesterone poses no such risk. For example, studies have shown that progesterone exhibits antimitotic activity in both breast and endometrial tissue (Chang, 1995, Fert. Steril. 63:785–791) and that women who experienced a deficiency of progesterone during their reproductive years were found to have a 5.4 fold increase in premenopausal breast cancer (Cowan et al., 1981, Am. J. Epidem. 114:209–217).

The route of administration of the hormone-containing cream of the invention is also advantageous in that it reduces the production of unwanted metabolites and provides a remarkably steady state of circulating hormone levels (Padwick et al., 1986, Fert. Steril. 46:402–407). This is accomplished in large part by avoiding the "first pass effect" through the enterohepatic circulation (see Lobo, 1994, Am. J. Obst. Gynecol. 170:1499–1507). In addition, transdermal application of native hormones would not induce SBG and thereby lower circulating androgen levels, as occurs following oral administration of currently prescribed synthetic hormones.

The novel feature of the invention, whereby application is rotated between different sites, prevents skin irritation. In fact, the hormone-containing cream is an excellent moisturizer and may have anti-wrinkle activity.

The psychological barriers presented by taking a "medication" are also lowered substantially by the fact that the hormones are self-administered and naturally occurring. It is expected that the instant invention will increase the use of hormone replacement therapy through enhanced patient and physican compliance, and will positively impact the health and well being of women worldwide.

What is claimed is:

1. A method of hormone replacement therapy, said method comprising administering to the skin of a patient in need of said therapy a physiologically acceptable formulation comprising native estrogen, native progesterone, and native testosterone in a ratio, by weight, of 1–5:10–500:1–5, in concentrations sufficient to raise circulating hormone levels to values found in the early luteal phase in premenopausal ovulatory women.

2. The method of claim 1, wherein said estrogen is estradiol, estrone, or estriol.

3. The method of claim 1, wherein said formulation further comprises dehydroepiandrosterone.

4. The method of claim 1, wherein said administration is begun at around the time of menopause.

5. A physiologically acceptable formulation comprising native estrogen, native progesterone, and native testosterone in a ratio, by weight, of 1–5:10–500:1–5, whereby administering said formulation to the skin of a patient in need thereof is sufficient to raise circulating estrogen, progesterone, and testosterone levels to values found in the early luteal phase in premenopausal ovulatory women.

6. The cream of claim 5, wherein said estrogen, progesterone and testosterone are synthesized from compounds obtained from a plant source.

7. The formulation of claim 5, wherein said formulation further comprises dehydroepiandrosterone.

8. The method of claim 1, whereby said circulating hormone levels are raised to at least 60 pg/ml estrogen, 1 ng/ml progesterone, and 30 pg/ml testosterone.

9. The method of claim 1, wherein said formulation comprises native estrogen, native progesterone, and native testosterone in a ratio, by weight, of 1–3:300–500:1–3.

10. The formulation of claim 5, said formulation comprising native estrogen, native progesterone, and native testosterone in a ratio, by weight, of 1–3:300–500:1–3.

11. A physiologically acceptable formulation comprising native estrogen, native progesterone, and native testosterone in concentrations of 0.5–1.5 mg/ml, 150–250 mg/ml, and 0.5–1.5 mg/ml, respectively, whereby administering said formulation to the skin of a patient in need thereof is sufficient to raise circulating estrogen, progesterone, and testosterone levels to values found in the early luteal phase in premenopausal ovulatory women.

12. The formulation of claims 5 or 11, wherein said formulation is a cream.

13. The method of claim 1, wherein said formulation is a cream.

14. The method of claim 1, wherein said formulation is administered to an area in which thin skin overlies fatty tissue.

15. The method of claim 14, wherein said formulation is administered to the lower abdomen, inner thigh, hip, or upper inner arm.

16. The method of claim 1, wherein said formulation comprises native estrogen, native progesterone, and native testosterone in concentrations of 0.5–1.5 mg/ml, 150–250 mg/ml, and 0.5–1.5 mg/ml, respectively, and 1/16 to 1/2 teaspoon of said formulation is administered to the skin.

17. The method of claim 1, wherein said formulation is administered 1–3 times per day.

18. The method of claim 8, whereby said progesterone level is raised to at least 2.5 ng/ml.

19. The formulation of claim 11, wherein said administration is sufficient to raise circulating estrogen to 40 pg/ml, circulating progesterone to at least 1 ng/ml, and circulating testosterone to greater than 30 ng/dl.

20. The formulation of claim 19, wherein said administration is sufficient to raise circulating progesterone to 2.5 ng/ml.

* * * * *

UNITED STATES PATENT AND TRADEMARK OFFICE
CERTIFICATE OF CORRECTION

PATENT NO.    : 6,228,852 B1
DATED         : May 28, 2001
INVENTOR(S)   : Carolyn V. Shaak Page 1 of 1

It is certified that error appears in the above-identified patent and that said Letters Patent is hereby corrected as shown below:

Column 1,
Line 61, delete "Gynaecol" and replace with -- Gynecol --

Column 2,
Line 33, delete "feminity" and replace with -- femininity --

Column 5,
Table 1, in the row starting with "Testosterone", please delete all entries of "pg/dl" and replace with -- ng/dl --
Lines 26-27, delete "30-50 nmol/ml" and replace with -- 30-50 ng/dl --

Column 7,
Line 9, delete "60" and replace with -- 40 --
Line 9, delete "estrogen, 1" and replace with -- estrogen, at least 1 --
Line 10, delete "and 30 pg/ml" and replace with -- and greater than 30 ng/dl --

Signed and Sealed this

Twenty-fourth Day of September, 2002

Attest:

Attesting Officer

JAMES E. ROGAN
Director of the United States Patent and Trademark Office